United States Patent [19]

Evans et al.

[11] Patent Number: 5,906,920
[45] Date of Patent: May 25, 1999

[54] METHODS FOR THE DETECTION OF LIGANDS FOR RETINOID X RECEPTORS

[75] Inventors: Ronald M. Evans; Ira G. Schulman, both of La Jolla, Calif.

[73] Assignee: The Salk Institute for Biological Studies, La Jolla, Calif.

[21] Appl. No.: 08/520,637

[22] Filed: Aug. 29, 1995

[51] Int. Cl.$^6$ .......................... G01N 33/53; G01N 33/566
[52] U.S. Cl. .......................... 435/7.1; 435/7.2; 435/7.21; 435/69.1
[58] Field of Search .............................. 530/350; 435/7.1, 435/69.1, 7.2, 7.21

[56] References Cited

PUBLICATIONS

Katzung, B.G. (1992) Basic and Clinical Pharmacology, 5th Editition, Appleton & Lange, Norwalk, Connecticut, p. 10 1992.

Lala et al. (1996) Nature 383: 450–453, Oct. 3, 1996.

Allan et al., "Hormone and Antihormone Induce Distinct Conformational Changes Which are Central to Steroid Receptor Activiation" J. Biol. Chem. 267:19513–19520 (1992).

Allegretto et al., "Transactivation Properties of Retinoic Acid and Retinoid X Receptors in Mammalian Cells and Yeast" J. Biol. Chem. 268(35):26625–26633 (1993).

Baniahmad et al., "Interaction of human thyroid hormone receptor β with transcription factor TFIIB may mediate target gene deression and activation by thyroid hormone" Proc. Natl. Acad. Sci. USA 90:8832–8836 (1993).

Baniahmad et al., "The τ4 Activation Domain of the Thyroid Hormone Receptor is Required for Release of a Putative Corepresser (s) Necessary for Transcriptional Silencing" Mol. Cell. Biol. 15(1):76–86 (1995).

Barettino et al., "Characterization of the ligand–dependent transactivation domain of thyroid hormone receptor" EMBO J. 13(13):3039–3049 (1994).

Beekman et al., "Transcriptional Activation by the Estrogen Receptor Requires a Conformational Change in the Ligand Binding Domain" Mol. Endrocrinol. 7(10):1266–1274 (1993).

Berger et al., "Interaction of Glucocorticoid Analogues with the Human Glucocorticoid Receptor" J. Steroid Biochem. Molec. Biol. 41(3–8):733–738 (1992).

Berkenstam et al., "Cooperativity in Transactivation Between Retinoic Acid Receptor and TFIID Requires an Activity Analogous to E1A" Cell 69:401–412 (1992).

Blanco et al., "Transcription factor TFIIB and the vitamin D receptor cooperatively activate ligand–dependent transcription" Proc. Natl. Acad. Sci. USA 92:1535–1539 (1995).

Cavaillès et al., "Interaction of proteins with transcriptionally active estrogen receptors" Proc. Natl. Acad. Sci. USA 91:10009–10013 (1994).

Cress and Triezenberg, "Critical Structural Elements of the VP16 Transcriptional Activation Domain" Science 251:87–90 (1991).

Danielian et al., "Identification of a conserved region required for hormone dependent transcriptional activation by steroid hormone reeptors" EMBO J. 11(3):1025–1033 (1992).

Durand et al., "Activation function 2 (AF–2) of retinoic acid receptor and 9–cis retinoic acid receptor: presence of a conserved autonomous constitutive activating domain and influence of the nature of the response element on AF–2 activity" Embo J. 13(22) :5370–5382 (1994).

Durfee et al., "The retinoblastoma protein associates with the protein phosphatse type 1 catalytic subunit" Genes & Devel. 7:555–569 (1993).

Fields and Song, "A novel genetic system to detect protein–protein interactions" Nature 340:245–246 (1989).

Fondell et al., "Unliganded thyroid hormone receptor inhibits formation of a functional preinitiation comples: implications for active repression" Genes & Devel. 7:1400–1410.

Forman et al., "Unique Response Pathways Are Established by Allosteric Interactions among Nuclear Hormone Receptors" Cell 81:541–550 (1995).

Halachmi et al., "Estrogen Receptor–Associated Proteins: Possible Mediators of Hormone–Induced Transcription" Science 264:1455–1458 (1994).

Hoey et al., "Molecular Cloning and Functional Analysis of Drosophila TAF110 Reveal Properties Expected of Coactivators" Cell 72:247–260 (1993).

Hollenberg and Evans, "Multiple and Cooperative Trans–Activation Domains of the Human Glucocorticoid Receptor" Cell 55:899–906 (1988).

Ing et al., Members of the Steroid Hormone Receptor Superfamily Interact with TFIIB (S300–II) J. Biol. Chem. 267(25):17617–17623 (1992).

Jacq et al., "Human TAF$_{II}$30 is Present in a Distinct TAFIID Complex and is Required for Transcriptional Activation by the Estrogen Receptor" Cell 79:107–117 (1994).

Keegan et al., "Separation of DNA Binding from the Transcription Activating function of a Eukaryotic Regulatory Protein" Science 231:699–704 (1986).

(List continued on next page.)

Primary Examiner—Lila Feisee
Assistant Examiner—Michael Pak
Attorney, Agent, or Firm—Stephen E. Reiter; Gray Cary Ware & Freidenrich, LLP

[57] ABSTRACT

The retinoid X receptor (RXR) participates in a wide array of hormonal signaling pathways either as a homodimer or as a heterodimer with other members of the steroid/thyroid hormone superfamily of receptors. In accordance with the present invention, the ligand-dependent transactivation function of RXR has been characterized and the ability of RXR to interact with components of the basal transcription machinery has been examined. In vivo and in vitro experiments indicate the RXR ligand binding domain makes a direct, specific and ligand-dependent contact with a highly conserved region of the TATA binding protein (TBP). The ability of mutations that reduce ligand-dependent transcription by RXR to disrupt the RXR-TBP interaction in vivo and in vitro suggests that RXR makes direct contact with the basal transcription machinery in order to achieve activation.

8 Claims, 5 Drawing Sheets

OTHER PUBLICATIONS

Kerr et al., "Association between proto–oncoprotein Rel and TATA–binding protein mediates transcriptional activation by NF–κB" *Nature* 365:412–419 (1993).

Lee et al., "Interaction of thyroid–hormone receptor with a conserved transcriptional mediator" *Nature* 374:91–94 (1995).

Lee et al., "Adenovirus E1A Activation Domain Binds the Basic Repeat in the TATA Box Transcription Factor" *Cell* 67:365–376 (1991).

Leid, M., "Ligand–induced Alteration of the Protease Sensitivity of Retinoid X Receptor α" *J. Biol. Chem.* 269(19):14175–14181 (1994).

Leng et al., "Mouse Retinold X Receptor Contains a Separable Ligand–Binding and Transactivation Domain in its E Region" *Mol. Cell. Biol.* 15(1):255–263 (1995).

Luckow and Schutz, "CAT constructions with multiple unique restriction sites for the functional analysis of eukaryotic promoters and regulatory elements" *Nucleic Acids Res.* 15(13):5490 (1987).

MacDonald et al., "The Vitamin D Receptor Interacts with General Transcription Factor IIB" *J. Biol. Chem*, 270(9)::4748–4752 (1995).

Mangelsdorf et al., "Retinoid Receptors" *Recent Progress in Hormone Research* 48:99–121 (1993).

Metz et al., "A C–terminal domain in FosB, absent om FosB/SF and Fra–1, which is able to interact with the TATA binding protein, is required for altered cell growth" *Embo J.* 13(16):3832–3842 (1994).

Oro et al., "Relationship between the product of the *Drosophila ultraspiracle* locus and the vertebrate retinoid X receptor" *Nature* 347:298–301 (1990).

Parker, M.G., "Steroid and related receptors" *Curr. Opin. in Cell Biol.* 5:499–504 (1993).

Schulman et al., "Interactions between the retinoid X receptor and a conserved region of the TATA–binding protein mediate hormone–dependent transactivation" *Proc. Natl. Acad. Sci. USA* 92:8288–8292 (1995).

Sikorski and Hieter, "A System of Shuttle Vectors and Yeast Host Strains Designed for Efficient Manipulation of DNA in *Saccharomyces cerevisiae*" *Genetics* 122:19–27 (1989).

Stunnenberg, H.G., "Mechanisms of Transactivation by Retinoic Acid Receptors" *Bioessays* 15 (5):309–315 (1993).

Tone et al., "Functional Analysis of a Transactivation Domain in the Thyroid Hormone β Receptor" *J. Biol. Chem.* 269(49):31157–31161 (1994).

Toney et al., "Conformational Changes in Chicken Thyroid Hormone Receptor α1 Induced by Binding to Ligand or to DNA" *Biochemistry* 32:2–6 (1993).

Umesono et al., "Direct Repeats as Selective Response Elements for the Thyroid Hormone, Retinoic Acid, and Vitamin $D_3$ Receptors" *Cell* 65:1255–1266 (1991).

Webster et al., "The Yeast $UAS_G$ is a Transcriptional Enhancer in Human HeLa Cells in the Presence of the GAL4 Trans –Activator" *Cell* 52:169–178 (1988).

Webster et al. "The Hormone–Binding Domains of the Estrogen and Glucocorticoid Receptors Contain an Inductible Transcription Activation Function" *Cell* 54:199–207 (1988).

Yao et al., "Drosophila ultraspiracle Modulates Ecdysone Receptor Function via Heterodimer Formation" *Cell* 71:63–72 (1992).

Zhang et al., "Mutations that Alter Ligand–Induced Switches and Dimerization Activities in the Retinoid X Receptor" *Mol. Cell. Biol.* 14:4311–4323 (1994).

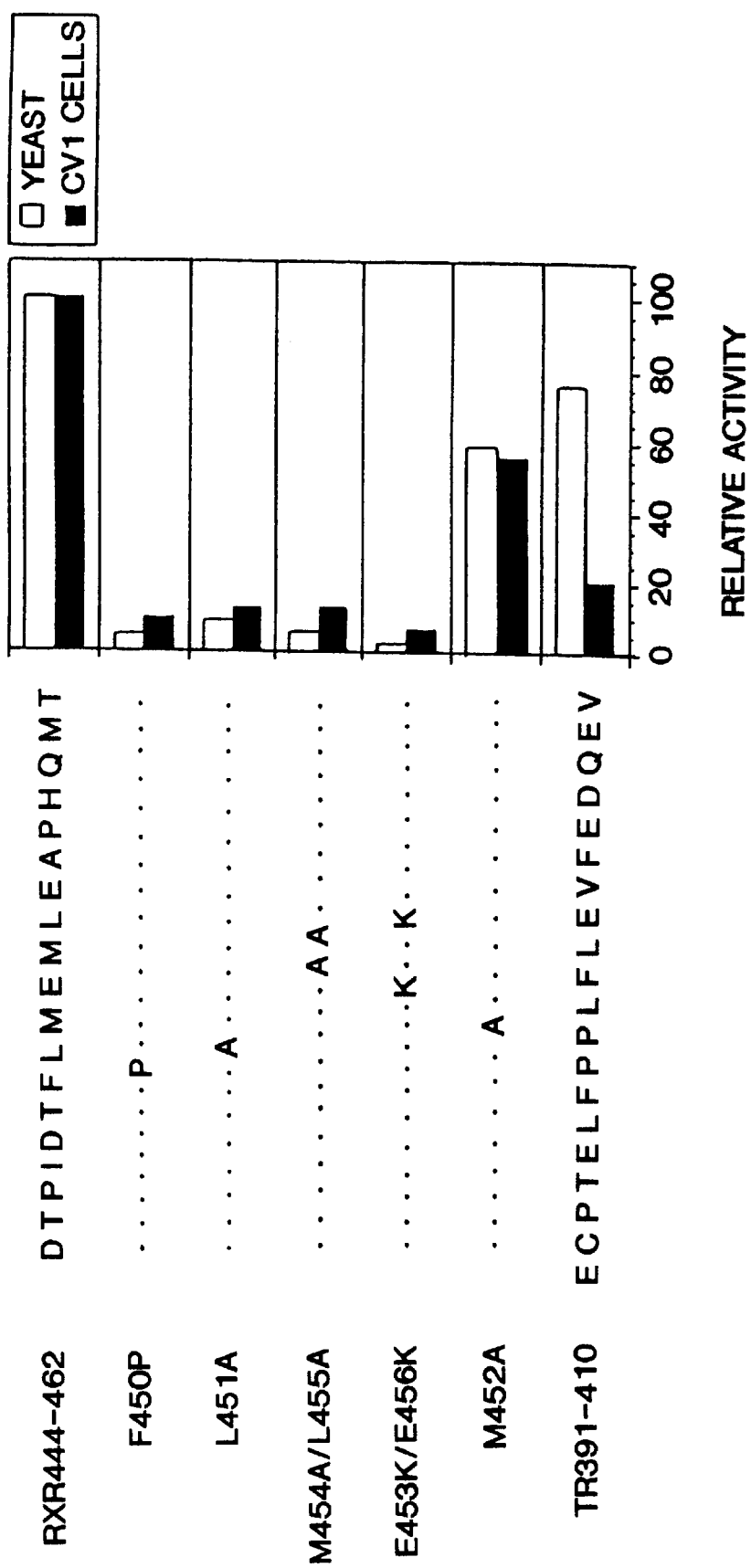

METHODS FOR THE DETECTION OF LIGANDS FOR RETINOID X RECEPTORS

ACKNOWLEDGEMENT

This invention was made with Government support under Grant No. GM 26444, awarded by the National Institutes of Health. The Government has certain rights in the invention.

FIELD OF THE INVENTION

The present invention relates to methods for the modulation of nuclear receptor mediated processes. In a particular aspect, the present invention relates to methods for the identification of compounds useful for such modulation, as well as compositions useful for such assays.

BACKGROUND OF THE INVENTION

Members of the steroid/thyroid hormone superfamily of receptors regulate expression of complex gene networks involved in vertebrate development, differentiation and homeostasis. A defining characteristic of these receptors lies in part in their ability to function as ligand-activated transcription factors. Retinoid X receptors (RXRs) occupy a central position in the function and activity of many members of this superfamily of receptors. For example, by forming heterodimers with retinoic acid receptors (RARs), thyroid hormone receptors (TRs), vitamin D receptors (VDRs), peroxisome proliferator activated receptors (PPARs) and several orphan receptors, RXRs participate in a diverse array of signaling pathways (Mangelsdorf et al., *Recent Prog. in Hormone Res.* 48:99–121 (1993)). The ability of RXR homodimers to respond to 9-cis retinoic acid identifies still another signaling pathway influenced by this nuclear receptor. The critical role of RXRs in the function of nuclear receptors is further highlighted by the structural and functional conservation between vertebrate RXRs and the Drosophila nuclear receptor ultraspiricle (Oro et al., *Nature* 347:298–301 (1990); and Yao et al., *Cell* 71:63–72 (1992)).

The mechanism by which RXR (and other nuclear receptors) activates transcription is poorly understood. Numerous studies have defined two independent transactivation functions (tau domains; τ) in most members of the steroid/thyroid hormone superfamily of receptors. These activation functions include a constitutive activation function (τ1 or AF-1) present in the amino-terminal region and a ligand-dependent activation function (τc or AF-2) present in the carboxy-terminal 200–250 amino acids. The carboxy-terminal domain of nuclear receptors is complex, mediating ligand-dependent activation, receptor homo- and heterodimerization and ligand binding (Parker, M. G., *Curr. Opin. in Cell Biol.* 5:499–504 (1993); and Stunnenberg, H. G., *BioEassays* 15:309–315 (1993)). Binding of ligand is thought to induce a conformational change in receptors that leads to activation of transcription (Allan et al., *J. Biol. Chem.* 267:19513–19520 (1992); Beekman et al., *Mol. Endrocrinol.* 7:1266–1274 (1993); Toney et al., *Biochemistry* 32:2–6 (1993); Leid, M., *J. Biol. Chem.* 269:14175–14181 (1994)).

It is not currently known how activated receptors propagate their signals to the basal transcription machinery. Direct interactions between the basal transcription factor TFIIB and several nuclear receptors have been reported (Ing et al., *J. Biol. Chem.* 267:17617–17623 (1992); Baniahmad et al., *Proc. Natl. Acad. Sci. USA* 90:8832–8836 (1993); Fondell et al., *Genes & Devel.* 7:1400–1410 (1993); Blanco et al., *Proc. Natl. Acad. Sci. USA* 92:1535–1539 (1995); and MacDonald et al., *J. Biol. Chem.* 270:4748–4752 (1995)). The nuclear receptor-TFIIB interaction does not appear to be influenced by ligand. Indeed, it has been suggested that interaction between TR and TFIIB may be associated with transcriptional repression (Baniahmad et al., (1993) supra; and Fondell et al., supra). The identification of several novel proteins suggested to be involved in ligand-activated transcription by nuclear receptors (Halachmi et al., *Science* 264:1455–1458 (1994); Jacq et al., *Cell* 79:107–118 (1994); Berkanstam et al., *Cell* 69:401–412 (1992); Cavailles et al., *Proc. Natl. Acad. Sci. USA* 91:10009–10013 (1994); and Lee et al., *Nature* 374:91–94 (1995)) suggests that coactivators or bridging factors may also be involved in transmitting the signal from ligand activated receptors to the basal transcription apparatus.

In view of the limited understanding of how activated receptors propagate their signals to the basal transcription machinery, what is needed in the art is a better understanding of such signalling processes. The identification of components of the basal transcription machinery involved in such signalling would be of great value. The identification of such components would also facilitate the development of assays for novel ligands for nuclear receptors.

BRIEF DESCRIPTION OF THE INVENTION

In accordance with the present invention, we have identified components of the basal transcription machinery involved in RXR signalling. Further in accordance with the present invention, the ligand-dependent transactivation function of RXR has been characterized and the ability of RXR to interact with components of the basal transcription machinery has been examined. In vivo and in vitro experiments indicate the RXR ligand binding domain makes a direct, specific and ligand-dependent contact with a highly conserved region of the TATA binding protein (TBP). The ability of mutations that reduce ligand-dependent transcription by RXR to disrupt the RXR-TBP interaction in vivo and in vitro suggests that RXR makes direct contact with the basal transcription machinery in order to achieve activation.

Recently a small region at the carboxy terminus of RXR has been identified that is required for ligand-activated transcription (Durand et al., *EMBO J.* 13:5370–5382 (1994); Leng et al., *Mol. Cell. Biol.* 15:255–263 (1995); and Zhang et al., *Mol. Cell. Biol.* 14:4311–4323 (1994)). This activation domain (τc), which is conserved among most members of the steroid and thyroid hormone receptor superfamily (Danielian et al., *EMBO J.* 11:1025–1033 (1992)), functions as a constitutive activator when fused to a heterologous DNA binding domain. In accordance with the present invention, the transactivation properties of RXR have been examined in both mammalian and in *Saccharomyces cerevisiae* cells. The ability of the RXR τc domain to function in both mammalian cells and in *S. cerevisiae* suggests that activation pathways mediated by RXR are conserved. Both in vivo and in vitro experiments indicate the RXR τc domain mediates an interaction between the RXR ligand binding domain and the conserved carboxy-terminal domain of the TATA binding protein (TBP). Mutations in either the RXR τc domain or in TBP disrupt this interaction, suggesting that the RXR-TBP interaction plays a functional role in transactivation by RXR.

BRIEF DESCRIPTION OF THE FIGURES

FIGS. 1(A–B) illustrates the effect of point mutations in the RXR τc domain on the ability of RXR to induce transactivation.

FIG. 1A presents transactivation results with fusions between the GAL4 DNA binding domain and the last 19 amino acids of human RXRα (amino acids 444–462) and the last 20 amino acids of human TRα (amino acids 391–410). Bold letters identify the mutations introduced into the RXR444–462 sequence. Dotted lines indicate all other amino acids are identical to the RXR444–462 sequence. The activity of GAL4RXR444–462 was set at 100%.

FIGS. 2(A–D) presents results of the yeast two-hybrid assay to assess the interaction between receptor ligand binding domains and various components of the basal transcription machinery.

FIGS. 3(A–B) demonstrates that point mutations in the basic repeat of TBP disrupt the interaction with RXR in vivo.

DETAILED DESCRIPTION OF THE INVENTION

In accordance with the present invention, mutations of the ligand-dependent activation function (τc) of RXR are exploited to examine the role of this domain in ligand-dependent transactivation. The τc domain encodes a potential amphipathic alpha helix with hydrophobic and negatively charged faces. This domain is necessary for ligand-dependent activation of transcription by RXR and is sufficient to activate transcription when fused to a heterologous DNA binding domain in both mammalian cells and S. cerevisiae (see FIG. 1). Using both the yeast two-hybrid assay and in vitro GST pull-down experiments, the RXR ligand binding domain has been shown to make a direct and specific contact with the basic repeat present in the conserved carboxy-terminal domain of the TATA binding protein (TBP; see FIGS. 2 and 3). The ability of mutations in the τc domain that reduce the transactivation ability of RXR to disrupt the RXR-TBP interaction in vivo and in vitro suggests this interaction has functional significance.

Figure 2A:
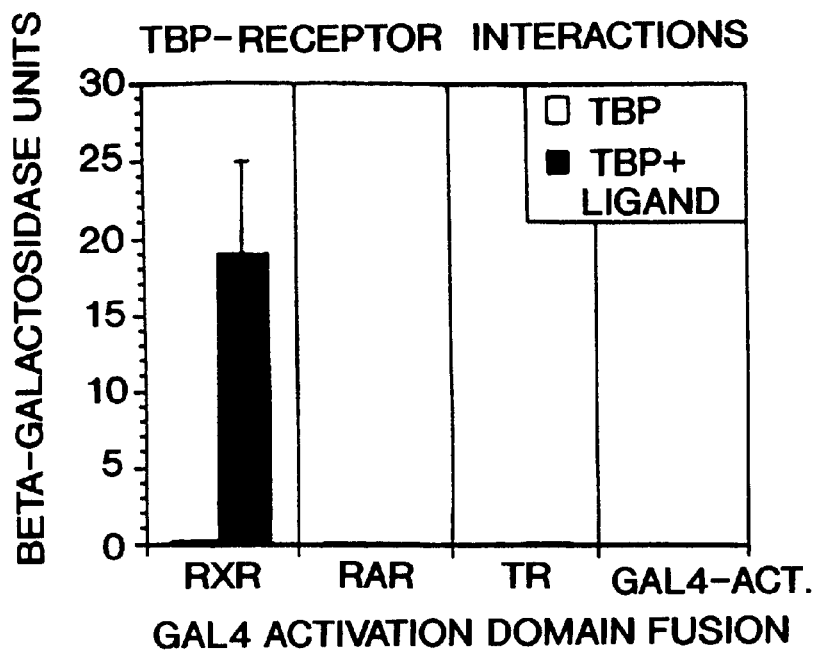
FIG. 2A presents results obtained employing fusions between the GAL4 activation domain and RXR, RAR, and TR; activation domain fusions were cotransformed into the strain Y190 along with fusions between the GAL4 DNA binding domain and the conserved carboxy terminal domain of human TBP. The results presented herein illustrate the interaction between receptor ligand binding domains and TBP. The activity of the GAL4 activation domain alone was measured only in the absence of ligand. Beta-galactosidase activity was measured after growth for 16 hours in the presence (filled bars) or absence (open bars) of 1 μM 9-cis retinoic acid (RXR and RAR) or 1 μM TRIAC (TR). No interaction between receptor and TBP is detected in the absence of ligand.
Figure 2B:
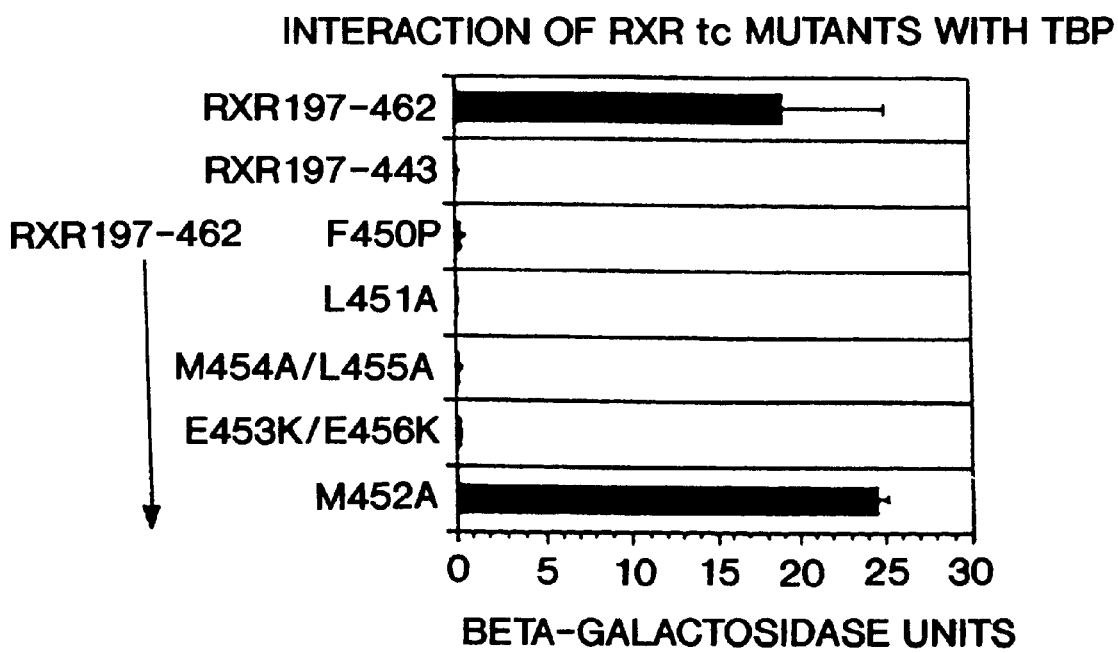
FIG. 2B illustrates the interaction between RXR ligand binding domain mutants and TBP. Only activity in the presence of 9-cis retinoic acid is shown. No interaction between the mutants and TBP is detected in the absence of 9-cis retinoic acid. Point mutants consist of amino acids 197–462 of RXR. RXR197–443 represents the τc truncation.

Both RXR and TR interact with a second component of the TFIID complex, TAF110 (see FIG. 2B). The finding that a functional τc domain is not required for the RXR-TAF110 interaction (see FIG. 2C) indicates the TAF110 interaction is not sufficient for activation of transcription. Nevertheless, the ability of RXR to interact with two members of the TFIID complex that do not interact with each other (Hoey et al., Cell 72:247–260 (1993)) may be important for receptor function.

Accordingly, in accordance with the present invention, there are provided methods to identify compounds which are agonists or antagonists for retinoid X receptor (RXR). Invention method comprises:

contacting:
a first fusion protein comprising the GAL4 DNA binding domain, operatively associated with a transactivation dependent, ligand dependent component of the basal transcription machinery (or, alternatively, operatively associated with the RXR ligand binding domain),
a second fusion protein comprising the GAL4 activation domain, operatively associated with the RXR ligand binding domain (or, alternatively, operatively associated with a transactivation dependent, ligand dependent component of the basal transcription machinery),
said putative agonist or antagonist for RXR, and
a reporter construct comprising a GAL4 response element operatively linked to a reporter gene;
contacting:
a third fusion protein comprising the GAL4 DNA binding domain (or, alternatively, the GAL4 activation domain), operatively associated with a transactivation independent, ligand dependent component of the basal transcription machinery,
said second fusion protein (or, alternatively, said first fusion protein),
said putative agonist or antagonist for RXR, and
said reporter construct; and thereafter
identifying as agonists those compounds which induce transactivation in the presence of both said transactivation dependent, ligand dependent component and said transactivation independent, ligand dependent component of the basal transcription machinery, identifying as antagonists those compounds which induce transactivation in the presence of said transactivation independent, ligand dependent component of the basal transcription machinery, but not in the presence of said transactivation dependent, ligand dependent component of the basal transcription machinery, and identifying those compounds which fail to induce transactivation in the presence of either said transactivation dependent, ligand dependent component or said transactivation independent, ligand dependent component of the basal transcription machinery as neither agonists nor antagonists of hormone-mediated pathways involving RXR.

Optionally, compounds which fail to induce transactivation in the presence of either said transactivation dependent, ligand dependent component or said transactivation independent, ligand dependent component of the basal transcription machinery can be further tested for the ability to bind RXR. Those compounds which do not bind are neither agonists nor antagonists of RXR, while those compounds which bind RXR (but fail to induce transactivation thereof in the presence of either of the above-described components of the basal transcription machinery) are presumably involved in other (i.e., non-hormone mediated) signalling pathways.

Various constructs employed in the practice of the present invention are well known in the art. Thus, the GAL4 DNA binding domain, the GAL4 activation domain, GAL4 resonse elements and various members of the basal transcription machinery have all been well characterized and extensively discussed in the art. For example, the DNA binding domain of the yeast GAL4 protein comprises at least the first 74 amino acids thereof (see, for example, Keegan et al., Science 231:699–704 (1986)). Preferably, the first 90 or more amino acids of the GAL4 protein will be used, with the first 147 amino acid residues of yeast GAL4 being presently most preferred.

The GAL4 fragment comprising the DNA binding domain employed in the practice of the present invention can be incorporated into any of a number of sites within the receptor protein. For example, the GAL4 DNA binding domain can be introduced at the amino terminus of the receptor protein, or the GAL4 DNA binding domain can be substituted for the native DNA binding domain of the receptor, or the GAL4 DNA binding domain can be introduced at the carboxy terminus of the receptor protein, or at other positions as can readily be determined by those of skill in the art.

Exemplary GAL4 response elements are those containing the palindromic 17-mer:

5'-CGGAGGACTGTCCTCCG-3'    (SEQ ID NO:1), such as, for example, 17MX, as described by Webster et al., in Cell 52:169–178 (1988), as well as derivatives thereof. Additional examples of suitable response elements include those described by Hollenberg and Evans in Cell 55:899–906 (1988); or Webster et al. in Cell 54:199–207 (1988).

Numerous components of the basal transcription machinery have been described, e.g., TBP, TAF, TAF110, TFIIA, TFIIB, TFIID, TFIIE, TFIIF, TFIIH, SUG1, TRIP1, TIF1, and the like.

Exemplary transactivation dependent/ligand dependent components of the basal transcription machinery include the TATA binding protein (TBP), SUG1, TRIP1, and the like.

An exemplary transactivation independent, ligand dependent component of the basal transcription machinery is the TBP mutant, TAF110.

Reporter constructs contemplated for use in the practice of the present invention comprise:

(a) a promoter that is operable in the host cell, (b) a hormone response element, and (c) a DNA segment encoding a reporter protein,
wherein the reporter protein-encoding DNA segment is operatively linked to the promoter for transcription of the DNA segment, and
wherein the hormone response element is operatively linked to the promoter for activation thereof.

Hormone response elements contemplated for use in the practice of the present invention are composed of at least one direct repeat of two or more half sites separated by a spacer of one nucleotide. The spacer nucleotide can be selected from any one of A, C, G or T. Each half site of response elements contemplated for use in the practice of the invention comprises the sequence

-RGBNNM-, wherein

R is selected from A or G;

B is selected from G, C, or T;

each N is independently selected from A, T, C, or G; and

M is selected from A or C;

with the proviso that at least 4 nucleotides of said -RGBNNM- sequence are identical with the nucleotides at corresponding positions of the sequence -AGGTCA-. Response elements employed in the practice of the present invention can optionally be preceded by $N_x$, wherein x falls in the range of 0 up to 5.

Presently preferred response elements contain at least one copy (with one, two or three copies most common) of the minimal sequence:

AGGACA A AGGTCA    (SEQ ID NO:2).

As noted above, the minimal sequence can optionally be flanked by additional residues, for example, as in the sequence:

GGACC AGGACA A AGGTCA CGTTC    (SEQ ID NO:3).

Exemplary reporter genes include chloramphenicol transferase (CAT), luciferase (LUC), beta-galactosidase (β-gal), and the like. Exemplary promoters include the simian virus (SV) promoter or modified form thereof (e.g., ΔSV), the thymidine kinase (TK) promoter, the mammary tumor virus (MTV) promoter or modified form thereof (e.g., ΔMTV), and the like [see, for example, Mangelsdorf et al., in Nature 345:224–229 (1990), Mangelsdorf et al., in Cell 66:555–561 (1991), and Berger et al., in J. Steroid Biochem. Molec. Biol. 41:733–738 (1992)].

As used herein in the phrase "operative response element functionally linked to an operative reporter gene", the word "operative" means that the respective DNA sequences (represented, for example, by the terms "GAL4 response element" and "reporter gene") are operational, i.e., work for their intended purposes; the word "functionally" means that after the two segments are linked, upon appropriate activation by a ligand-receptor complex, the reporter gene will be expressed as the result of the fact that the "GAL4 response element" was "turned on" or otherwise activated.

Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "Physiological conditions" are readily understood by those of skill in the art to comprise an isotonic, aqueous nutrient medium at a temperature of about 37° C.

In the invention assay, the RXR-TBP interaction is ligand-dependent. Invention assays and transactivation experiments are carried out with ligand concentrations well above the $K_d$ values for LG69 and 9-cis retinoic acid (Allegretto et al., *J. Biol. Chem.* 268:26625–26633 (1993)) such that small changes in ligand affinity would not be expected to have significant effects. The ability of RXR τc domain mutants to interact in a ligand-dependent fashion with TAF110 (see FIG. 2D) and to bind ligand in vitro indicates that the absence of an interaction between the mutants and TBP does not result from a defect in ligand binding.

Taken together, these results suggest the RXR τc domain directly interacts with TBP and that this interaction is regulated by ligand. This conclusion is supported by the in vitro interaction between the GAL4-τc domain fusion and TBP. Finally, the ability to recover the interaction between the RXR τc domain mutant and TBP by introducing a second site mutation in TBP (see FIG. 3B) further supports the conclusion that the τc domain directly interacts with TBP. The ability of multiple factors to contact the basic repeat of TBP suggests that interaction with this domain of TBP may represent a common mechanism for transactivation.

The observation that RAR and TR do not interact with TBP (see FIG. 2A) suggests that different RXR/nuclear receptor heterodimers may activate transcription by contacting different components of the transcriptional machinery. This conclusion is consistent with the observation that ligand responsiveness of RXR can be modified by heterodimeric pairing. The ability of mutations in the RXR τc domain to adversely effect transactivation by heterodimers suggests that when complexed as a heterodimer, the RXR τc domain can be redirected to a different coactivator or component of the basal transcription machinery.

In accordance with another embodiment of the present invention, there are provided RXR mutants which retain the ability to bind 9-cis-retinoic acid, but which are not activated by 9-cis-retinoic acid. Examples of such mutants include RXR mutant D444A, RXR mutant T445A, RXR mutant P446A, RXR mutant I447A, RXR mutant D448A, RXR mutant T449A, RXR mutant F450P, RXR mutant L451A, RXR double mutant M454A, L455A, RXR double mutant E453K, E456K, RXR mutant M452A, and the like.

In accordance with yet another embodiment of the present invention, there are provided methods to identify agonists of retinoid X receptors. Invention method comprises:

contacting cells containing an RXR mutant as described above (i.e., having the ability to bind 9-cis-retinoic acid, but lacking the ability to be activated by 9-cis-retinoic acid) with a putative RXR ligand, wherein said cells contain an RXR response element operatively linked to a reporter gene, and thereafter monitoring the expression of reporter gene product.

In an alternate aspect of this embodiment, there are also provided methods to identify antagonists of retinoid X receptors. This method comprises:

contacting cells containing an RXR mutant (as described above) with a constant amount of an RXR agonist and variable amounts of a putative antagonist therefor, wherein said cells contain an RXR response element operatively linked to a reporter gene, and thereafter monitoring the expression of reporter gene product as a function of the amount of putative antagonist administered to said test cell.

In accordance with yet another embodiment of the present invention, there are provided methods to detect ligand-dependent interactions between retinoid X receptor and one or more components of the basal transcription machinery. Invention methods comprise:

contacting:

a first fusion protein comprising the GAL4 DNA binding domain, operatively associated with a first component of the basal transcription machinery (or, alternatively, operatively associated with the RXR ligand binding domain), a second fusion protein comprising the GAL4 activation domain, operatively associated with the RXR ligand binding domain (or, alternatively, operatively associated with a first component of the basal transcription machinery), an RXR ligand, and a reporter construct comprising a GAL4 response element operatively linked to a reporter gene; and thereafter monitoring for expression of said reporter.

In accordance with a further aspect of this embodiment of the present invention, the above-described contacting and monitoring steps can be repeated, employing a different first fusion protein (or different second fusion protein) which differs from the original first (second) fusion protein by containing a different component of the basal transcription machinery than the original first (second) fusion protein. This added step allows one to identify both transcription dependent/ligand dependent and transcription independent/ligand dependent components of the basal transcription machinery, which are useful for conducting the above-described assays.

The invention will now be described in greater detail by reference to the following non-limiting examples.

EXAMPLE 1

Preparation of plasmids

For integration in *S. cerevisiae*, plasmid pRS305CYH was constructed by cloning a BglII-SalI fragment from pAS1-CYH2 (gift of S. Elledge, Baylor College of Medicine) containing the ADH promoter, GAL4 DNA binding domain (amino acids 1–147), influenza hemagglutinin epitope and poly linker in the order written into BamHI-SalI digested pRS305 (Sikorski and Hieter, *Genetics* 122:19–27 (1989)).

For expression of GAL4-DNA binding domain fusions of human TBP mutants in *S. cerevisiae* (see below), plasmid pG6H was constructed by PCR amplification of the GAL4 DNA binding domain-influenza hemagglutinin epitope-polylinker from pAS1-CYH2. A sequence encoding six histidines was included directly after the initiator methionine of GAL4 in the 5' oligonucleotide. The amplified product was ligated into BamHI digested pG-1 (Schena et al., In: *Vectors for constitutive and inducible gene expression in yeast*, Guthrie and Fink (eds.), (Academic Press, Inc., San Diego) pp. 389–398 (1991)).

For expression of GAL4-DNA binding domain fusions in CV1 cells, the plasmid pCMXG4epi was constructed by PCR amplification of the GAL4 DNA binding domain-influenza hemagglutinin epitope-poly linker from pAS1-CHY2 and cloning into HindIII-BamHI digested pCMX (Umesono et al., *Cell* 65:1255–1266 (1991)). An optimal mammalian translation initiation sequence was included in the 5' oligonucleotide and introduced into the amino terminus of GAL4.

Receptor ligand binding domain fusions were cloned by PCR amplification of human RXRα (amino acids 197–462), human RARα (amino acids 186–462) and human TRα (amino acids 121–410). A ligand binding domain fusion with truncation of the τc domain (RXR197–443) was amplified as described above, however, an in-frame stop condon was introduced into the 3' oligonucleotide at the appropriate position.

For τc domain fusions, amino acids 444–462 of human RXRα and 391–410 of human TRα were amplified by PCR. Point mutations were introduced into the RXR τc domain by PCR using oligonucleotides with the appropriate base changes. Amplified products were ligated into NcoI-BamHI digested pRS305CYH. For expression in CV1 cells, appropriate restriction fragments from the pRS305CYH clones were subcloned into pCMXG4epi.

For two-hybrid assays, GAL4-activation domain fusions of RXR, RAR and TR were constructed by cloning the same amplification products described above into NcoI-BamHI digested pACTII (S. Elledge, Baylor College of Medicine; see Durfee et al., in *Genes & Development* 7:555–569 (1993)).

GAL4-DNA binding domain fusions expressing the C-terminal domain of human TBP (pAS+h180c), full length Drosophila TAF110 and full length Drosophila TAF40 (pAS+dTAF40) were provided by G. Gill and R. Tjian (UC Berkeley; see Hoey et al., in *Cell* 72:247–260 (1993)). Human TBP (amino acids 155–335) was amplified by PCR in two fragments. Point mutations were introduced into the appropriate oligonucleotides. After PCR, the two fragments were cloned into NcoI/BamHI digested pG6H. A GAL4-DNA binding domain fusion of human TFIIB was made by PCR amplification of the human cDNA and cloned into the BamHI site of pG6H.

GST-RXR197–462 was constructed by PCR amplification of the appropriate sequences from human RXRα. The amplification products were cloned into EcoRI-BamHI digested pGEX2TK. All PCR-derived constructs were verified by sequencing. The plasmid pGEX-TBP was the kind gift of Dr. I. Verma (Salk Institute; see Kerr et al., in *Nature* 365:412–419 (1993)). Mammalian expression constructs expressing the ligand biding domains of human RXRα, human RARα and human TRβ have been described elsewhere (Forman et al., *Cell* 81:541–550 (1995)).

The luciferase reporter GAL3-TK-LUC containing three binding sites for GAL4 upstream of the TK promoter luciferase fusion was the gift of Dr. P. N. Rangarajan. GAL3-TK-LUC contains three copies of double-stranded GAL4 reponse element, cloned upstream of the TK promoter of TK-LUC at the HindIII site. TK-LUC is prepared as follows: the MTV-LTR promoter sequence was removed from the MTV-LUC plasmid described by Hollenberg and Evans in *Cell* 55:899–906 (1988) by HindIII and XhoI digest, and cloned with the HindIII-XhoI fragment of the Herpes simplex virus thymidine kinase gene promoter (–105 to +51 with respect to the transcription start site, m, isolated from plasmid pBLCAT2, described by Luckow & Schutz in *Nucleic Acids Res.* 15:5490 (1987)) to generate parental construct TK-LUC.

EXAMPLE 2

Yeast Strains and Methods

The strain Y190 (MATa gal4 gal80 his3 trpl-901 ade2–101 ura3–52 leu2–3,-112 cyh$^r$ URA3::GAL1→lacZ LYS2::GAL1→HIS3; a gift of S. Elledge, Baylor College of Medicine; Y190 is derived from Y153, described by Durfee et al., supra) was used for all experiments. For beta-galactosidase assays, a minimum of three independent transformants were grown overnight at 30° C. in minimal media (0.66% YNB, 2% glucose) supplemented with the appropriate amino acids. Cells were diluted 1:20 into fresh media and 9-cis retinoic acid of 3,3',5-triiodthyroacetic acid (TRIAC) was added if required. Beta-galactosidase activity was measured after 16 hours of growth at 30° C. as described by Rose et al., *Methods in yeast genetics* (Cold Spring Harbor Laboratory Press, Cold Spring Harbor) (1990).

EXAMPLE 3

Transfection

CV1 cells were plated in 48 well plates at a density of 2×10$^4$ cells/well in DMEM supplemented with 10% charcoal-resin split fetal bovine serum. After growth at 37° C. for 12–16 hours, cells were transfected using the DOTAP transfection reagent following the manufacturer's instructions (Boehringer Mannheim). For each well, 12 ng of GAL3-TK-LUC reporter, 36 ng of the appropriate expression constructs and as an internal control, 60 ng of pCMX-βgal DNA were transfected. DNA was introduced along with 200 μl of DMEM supplemented with 10% charcoal-resin split fetal bovine serum. Cells were incubated with DNA for 5 hours at 37° C. The media was then removed, the cells washed once with fresh media and 200 μl of media with or without 9-cis retinoic acid, T$_3$ (3,3',5-triiodo-L-thyronine) or vitamin D$_3$ was added. The RXR specific ligand LG69 (4-[1-(3,5,5,8,8-pentamethyl-5,6,7,8-tetrahydro-2-naphthyl-1-ethenyl]benzoic acid) and the RAR specific ligand AM580 (4-(5,6,7,8-tetrahydro-5,5,8,8-tetramethyl-2-napthamido) benzoic acid) were also used. Cells were harvested after 36 hours of growth at 37° C. Luciferase activity of each sample was normalized by the level of beta-galactosidase activity. Each transfection was carried out in duplicate and repeated at least three times. The fold induction reported is relative to the GAL3-TK-LUC reporter alone included in each experiment.

EXAMPLE 4

RXR-TBP interaction Assay

GST-fusion proteins were induced, solubilized and bound to glutathione beads following the manufacturer's procedures (LKB-Pharmacia). After binding to glutathione beads, 15 μl of the suspension was incubated with 1 to 2 μl of the appropriate $^{35}$S-labeled in vitro translated protein for 1 hour in 500 μl of NETN (20 mM Tris-HC1, pH 7.5, 100 mM KC1, 0.7 mM EDTA, 0.5% NP40, 1 mM PMSF). Following incubation, the beads were washed three times with NETN. Bound proteins were eluted with 20 μl of 1X SDS-PAGE buffer and electrophoretically separated in a SDS-10% polyacrylamide gel. The interaction of in vitro translated GAL4 fusions with GST-TBP was carried out using the above procedure with the following modifications. The initial interaction was carried out in NETN in which KC1 was replaced with 0.3 M NaC1 and non-fat dry milk was added to final concentration of 0.5% (w/v). Following incubation, the beads were washed three times with NETN in which the NaC1 concentration was increased to 0.5 M and non-fat dry milk was added to final concentration of 0.5% (w/v). Following fixation gels were treated with 1 M salicylic acid, dried and subjected to autoradiography.

EXAMPLE 5

Mutagenesis of the RXR τc domain

The carboxy terminal 19 amino acids of RXR and 20 amino acids of TR have been shown to activate transcription when fused to heterologous DNA binding domains (FIG. 1; (Durand et al., supra; Leng et al., supra; Zhang et al., supra; Baniahmad et al., *Mol. Cell. Biol.* 15:76–86 (1995); Barettino et al., *EMBO J.* 13:3039–3049 (1994); and Tone et al., *J. Biol. Chem.* 269:31157–31161 (1994)). This region has been proposed to form an amphipathic alpha helix with hydrophobic and negatively charged faces (Danielian et al., supra).

FIG. 1A presents transactivation results with fusions between the GAL4 DNA binding domain and mutants of the last 19 amino acids of human RXRα (amino acids 444–462) and the last 20 amino acids of human TRα (amino acids 391–410). These constructs were transfected into CV1 cells along with the reporter GAL3-TK-LUC or integrated into the genome of the *S. cerevisiae* strain Y190 containing the integrated GAL1-lacZ reporter as described above. CV1 cell transfection results were normalized by cotransfection with a beta-galactosidase expression plasmid. Western blotting of *S. cerevisiae* extracts indicates the GAL4 fusions are expressed at similar levels.

Mutation of the carboxy-terminal 19 amino acids of RXR (FIG. 1A) indicates that, like several other transactivation domains, the hydrophobic and acidic amino acids are critically important for function (Cress and Triezenberg, *Science* 251:87–90 (1991)). Within the hydrophobic face of the helix individual changes of phenylalanine at position 450 to proline (F450P), leucine at position 451 to alanine (L451A) and the double mutant methionine 454 to alanine/leucine 455 to alanine (M454A/L455A) severely reduce the ability of GAL4 fusions to activate transcription when assayed in the context of the isolated τc domain in both mammalian and *S. cerevisiae* cells. The double mutant glutamic acid 453 to lysine/glutamic acid 456 to lysine (E453K/E456K) on the charged face of the helix also eliminates the ability to the isolated τc domain to activate transcription (FIG. 1A). The single mutations E453K and E456K reduce transcription approximately 60–70%.

Figure 1B:
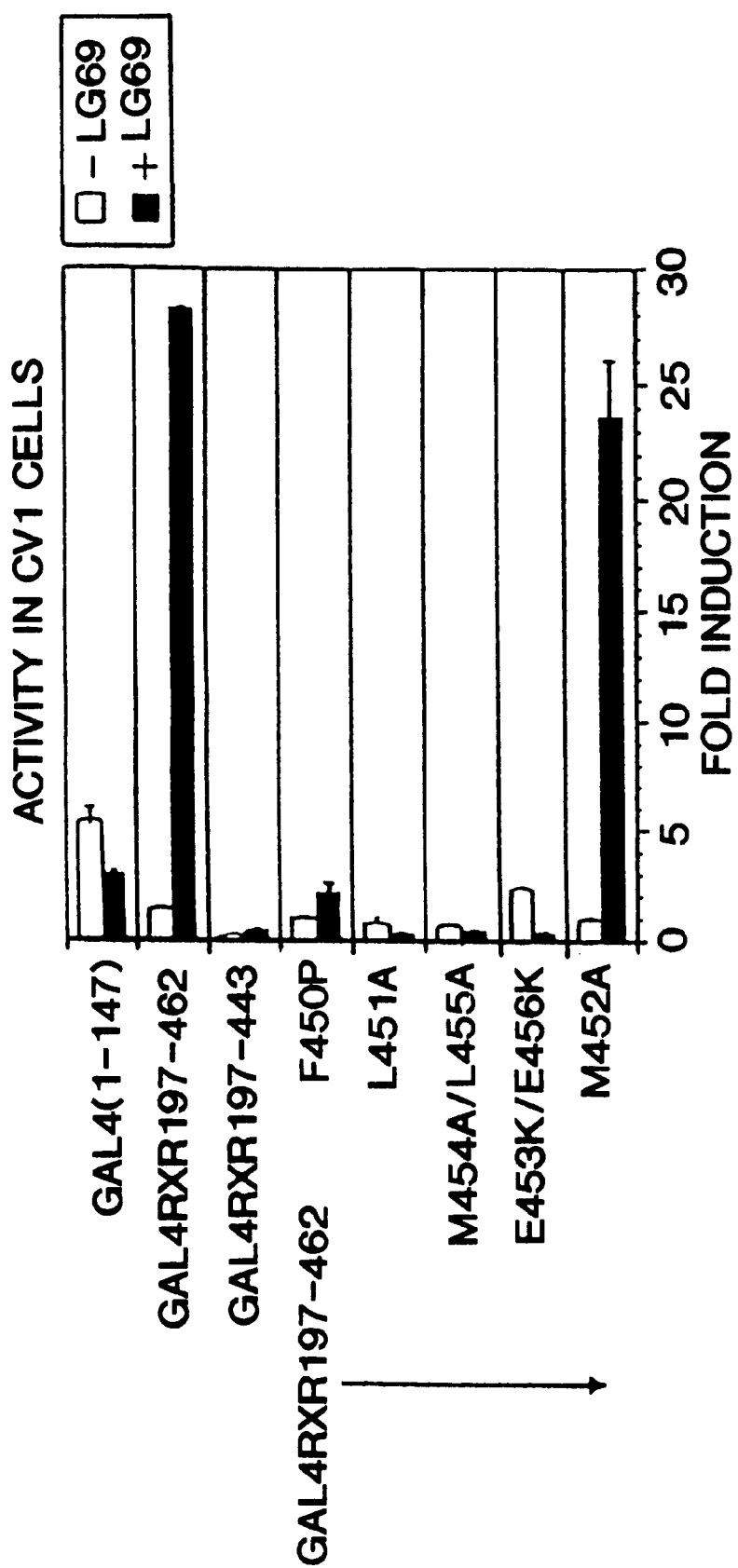
FIG. 1B presents transactivation results with constructs prepared by introducing the point mutations described in FIG. 1A into the GAL4-RXR ligand binding domain fusion (GAL4RXR197–462). GAL4RXR197–443 represents the τc truncation. After transfection, CV1 cells were cultured in the presence (filled bars) or absence (open bars) of 100 nM LG69 (an RXR specific ligand) for 36 hours. Fold induction relative to the reporter alone is reported.

Mutation of methionine 452 to alanine (M452A), however, has little effect. Incorporation of these same mutations into the complete ligand binding domain (FIG. 1B) or into full length receptors reduces the ability of these mutant RXRs to activate transcription in response to RXR specific ligands. Importantly, truncation of the 19 amino acids (GAL4RXR197–443) also produces a receptor that fails to activate transcription (FIG. 1B). The reduction in ligand-dependent transcription observed with GAL4RXR197–443 does not appear to result from a defect in ligand binding (see FIG. 2D). Taken together, the results confirm that the last 19 amino acids of RXR are both necessary and sufficient for transactivation and indicate that both the hydrophobic and charged faces of the helix residues are important for this function.

EXAMPLE 6

RXR interacts with the TATA binding protein

The finding that mutations in the RXR τc domain have qualitatively similar effects in mammalian and *S. cerevisiae* cells (FIG. 1A) suggests that RXR directly contacts a structurally and functionally conserved component of the transcription machinery. This observation is consistent with the finding that several other transcription factors, including members of the steroid and thyroid hormone receptor superfamily, interact with components of the basal transcription machinery (Ing et al., supra; Baniahmad et al., (1993) supra; Fondell et al., supra; Blanco et al., supra; and MacDonald et al., supra). Therefore, we examined the interactions between RXR and several basal transcription factors, including the TATA binding protein (TBP), TAF110, TAF40 and TFIIB, using the both yeast two-hybrid system (Fields and Song, *Nature* 340:245–246 (1989); and Durfee et al., *Genes & Devel.* 7:555–569 (1993)) and in vitro protein-protein interaction assays. As shown in FIG. 2A, the two-hybrid assay detects a specific and ligand-dependent interaction between RXR and the conserved carboxy-terminal domain of TBP.

Figure 2C:
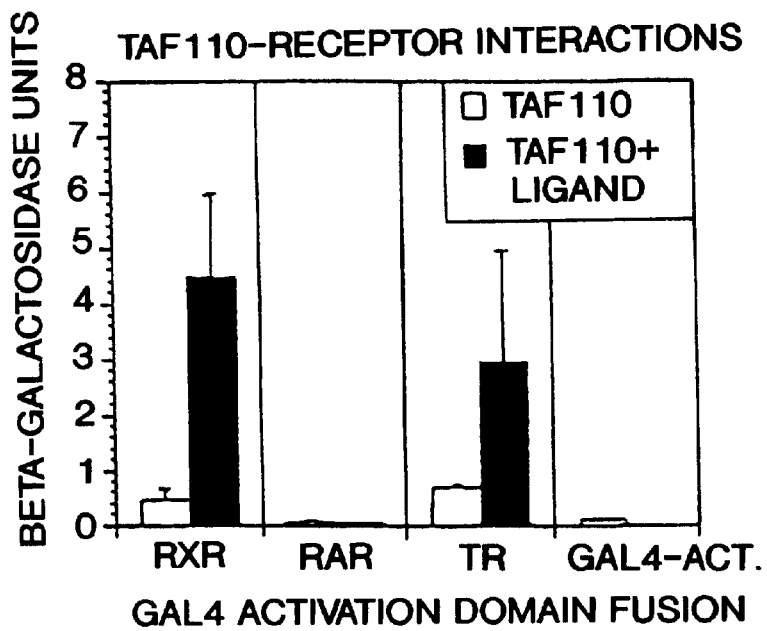
FIG. 2C repeats the experiments summarized in FIG. 2A, using full length Drosophila TAF110 in place of human TBP.
Figure 2D:
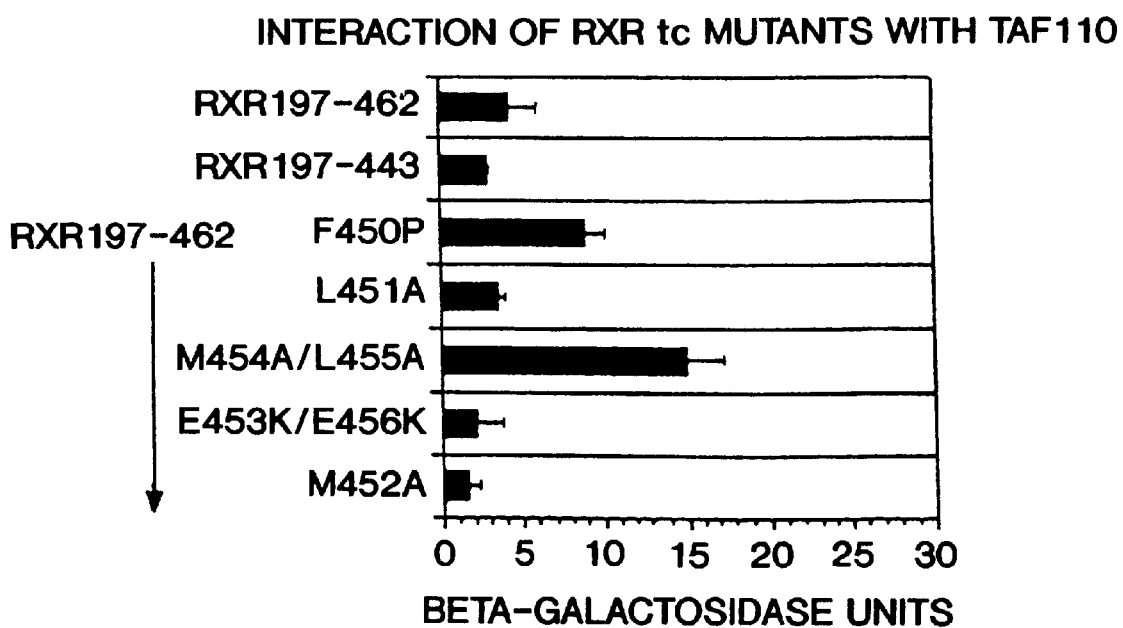
FIG. 2D illustrates the interaction between RXR ligand binding domain mutants and TAF110. Only activity in the presence of 9-cis retinoic acid is shown. No interaction between the mutants and TAF110 is detected in the absence of 9-cis retinoic acid.

Thus, fusions between the GAL4 activation domain and RXR, RAR, and TR and RXR τc mutants were cotransformed into the strain Y190 along with fusions between the GAL4 DNA binding domain and the conserved carboxy terminal domain of human TBP (see FIGS. 2A and 2B) or full length Drosophila TAF110 (see FIGS. 2C and 2D). Beta-galactosidase activity was measured after growth for 16 hours in the presence (filled bars) or absence (open bars) of 1 μM 9-cis retinoic acid (RXR and RAR) or 1 μM TRIAC (TR; see FIGS. 2A and 2C). Interaction between receptor ligand binding domains and TBP and TAF110 are shown in FIGS. 2A and 2C, respectively. The activity of the GAL4 activation domain alone was measured only in the absence of ligand. Note the difference in scale between FIGS. 2A and 2C.

The interaction between RXR ligand binding domain mutants and TBP and TAF110 are shown in FIGS. 2B and 2D, respectively. Only activity in the presence of 9-cis retinoic acid is shown. No interactions between the mutants and TBP or TAF110 is detected in the absence of 9-cis retinoic acid. Point mutants consist of amino acids 197–462 of RXR. RXR197–443 represents the τc truncation. Western blotting of *S. cerevisiae* extracts indicates the GAL4-activation domain fusions are expressed at similar levels. Interactions between TAF40 and RXR, RAR or TR were also tested and not detected. An interaction was detected between TR and TFIIB.

Mutations in the RXR τc domain that eliminate the ability of RXR to activate transcription (FIG. 1) eliminate a detectable interaction between RXR and TBP (FIG. 2B). Although TR and RAR have τc domains that exhibit significant sequence homology to the RXR τc domain, an interaction between TR or RAR and TBP is not detected (FIG. 2A). Nevertheless, the same region of TR activates transcription in *S. cerevisiae* when fused to the GAL4 DNA binding domain. The failure to detect an interaction between RAR and TBP or between TR and TBP suggests that transactivation by RXR homodimers may utilize different components of the transcription machinery than transactivation by RAR and TR heterodimers.

FIG. 2C also shows that RXR can make a ligand-dependent interaction with a second component of the TFIID complex, TAF110. The interaction between RXR and TAF110 is detectable even when τc domain mutants are analyzed, indicating the functional state of the τc domain is not important for the interaction (FIG. 2D). Nevertheless, the ability to detect ligand-dependent interactions between transcriptionally defective RXR mutants and TAF110 suggests that mutations in the RXR τc domain do not have large effects on ligand binding. The observation that TR (FIG. 2C) also interacts with TAF110 suggests this basal factor may be a common target for multiple nuclear receptors.

Although the results of the two-hybrid assay suggest RXR makes a direct protein-protein interaction with TBP, the possibility that this interaction is mediated by a conserved coactivator cannot be ruled out by this assay. To further characterize the interaction between RXR and TBP, the ability of TBP to interact in vitro with bacterial expressed glutathione-S-transferase RXR fusion proteins was examined.

Thus GST pull-down experiments were carried out as follows. TBP was in vitro transcribed and translated as described above, and incubated with equal amounts of immobilized GST-RXR197–462 or GST-RXR-E453K/E456K) as determined by coomassie stained gels. Following extensive washing of the beads, bound proteins were eluted and resolved by SDS-PAGE and the gel was processed for autoradiography. When added, 1.0 μM 9-cis retinoic acid was included in all buffers. Exposure time was 2 hours. Little or no interaction between TBP and GST alone is detected under these conditions.

Thus, the GST pull-down experiment shows a strong interaction between in vitro translated TBP and GST-RXR197–462. An in vitro interaction between GST-RXR197–462 and TAF110 is also observed. A mutation of the RXR τc domain (E453K/E456K) that eliminates the RXR-TBP interaction in the two-hybrid assay (FIG. 2B) reduces the in vitro interaction between RXR and TBP approximately 6 fold. Similar results are observed when a full length GST-RXR fusion is used.

A direct in vitro interaction between TBP and the τc domain itself (GAL4RXR444–462) that is sensitive to the functional state of the τc domain can also be detected, as follows. Equal amounts of in vitro translated GAL4RXR444–462, GAL4RXR444–462-E453K/E456K or GAL4(1–147) as determined by phosphorimaging analysis were incubated with immobilized GST-TBP or with immobilized GST. Following extensive washing of the beads, bound proteins were eluted and resolved by SDS-PAGE and the gel was processed for autoradiography. Exposure time was 7 hours. The sensitivity of the in vitro interactions to mutations in the RXR τc domain strongly suggests the τc domain mediates a direct interaction between RXR and TBP.

Unlike the two hybrid assay, a RXR-TBP interaction in vitro can be detected in the absence of ligand. Addition of ligand stimulates the interaction 3–5 fold when quantitated by phosphorimaging. The detection of ligand-independent interactions in vitro may result from the ability of the large amounts of protein used in vitro to stabilize a weak interaction that cannot be detected in the two-hybrid assay.

To further define the RXR-TBP interaction, mutations were introduced into well conserved amino acids present in the basic repeat of TBP and analyzed for interaction with RXR in the two-hybrid assay. This domain of TBP has been shown to be a common target of several transcription factors (Lee et al., *Cell* 67:365–376 (1991); Metz et al., *Mol. Cell. Biol.* 14:6021–6029 (1994a); and Metz et al., *EMBO J.* 13:3832–3842 (1994b)). Thus, a Fusion between the GAL4 activation domain and RXR (amino acids 197–462) was cotransformed into the strain Y190 along with fusions between the GAL4 DNA binding domain and human TBP (the conserved carboxy terminal domain, amino acids 151–335). Y233G, R321E/K232E/R235E, V236G and V237G identify the amino acid changes introduced into TBP. Beta-galactosidase activity was measured after growth for 16 hours in the presence of 1 μM 9-cis retinoic acid as described in Materials and Methods. Western blotting of *S. cerevisiae* extracts indicates the GAL4-TBP fusions were expressed in similar levels.

Figure 3A:
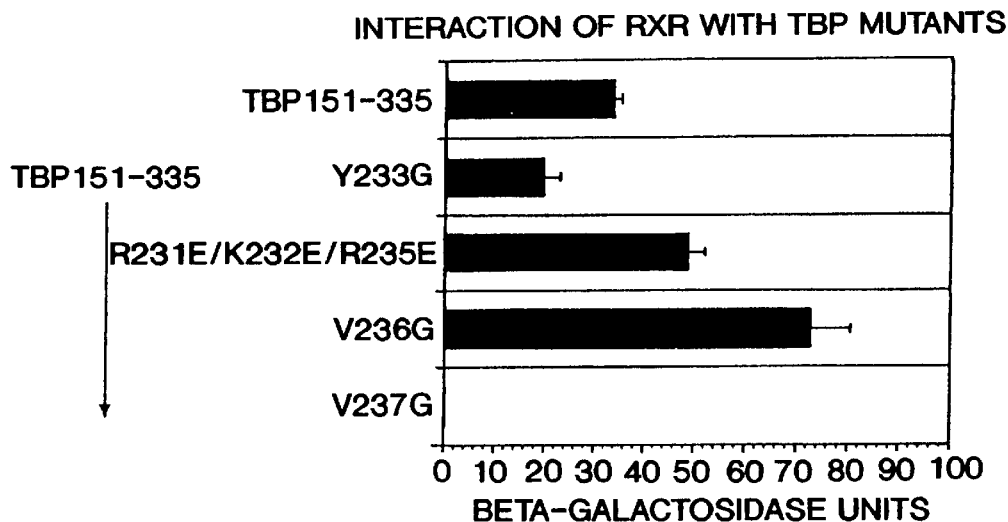
FIG. 3A presents results when a fusion between the GAL4 activation domain and RXR (amino acids 197–462) was cotransformed into a host (strain Y190) along with fusions between the GAL4 DNA binding domain and human TBP (the conserved carboxy terminal domain, amino acids 151–335). Y233G, R321E/K232E/R235E, V236G and V237G identify the amino acid changes introduced into TBP. Beta-galactosidase activity was measured after growth for 16 hours in the presence of 1 μM 9-cis retinoic acid as described in the Example section.

FIG. 3A shows that the TBP mutant V237G eliminates a detectable RXR-TBP interaction. Several other mutations in this region of TBP, including V236G, have no effect.

The finding that a single point mutation in TBP could disrupt the interaction with the wildtype RXR ligand binding domain prompted an examination of the ability of TBP-V237G to interact with the RXR τc mutants. Thus, fusions between the GAL4 activation domain and RXR τc mutants were cotransformed into the strain Y190 along with a fusion between the GAL4 DNA binding domain and the TBP mutants described in reference to FIG. 3A. Beta-galactosidase activity was measured after growth for 16 hours in the presence (filled bars) or absence (open bars) of 1 μM 9-cis retinoic acid as described above. Point mutants consist of amino acids 197–462 of RXR. RXR197–443 represents the τc truncation. Note the difference in scale between A and B.

Figure 3B:
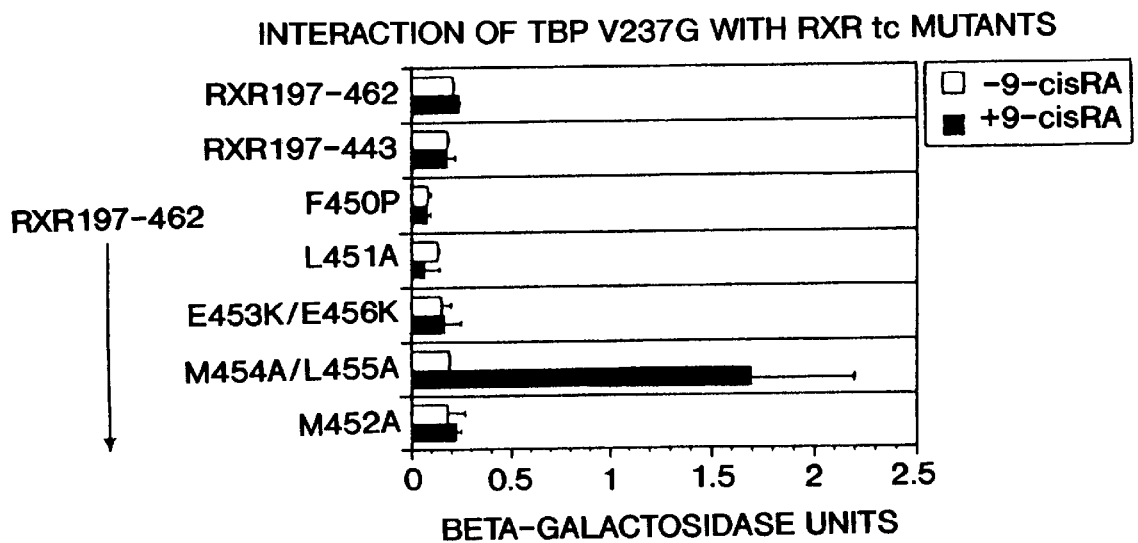
FIG. 3B presents results when fusions between the GAL4 activation domain and RXR τc mutants were cotransformed into a host (strain Y190) along with a fusion between the GAL4 DNA binding domain and the TBP mutant V237G described in reference to FIG. 3A. Beta-galactosidase activity was measured after growth for 16 hours in the presence (filled bars) or absence (open bars) of 1 μM 9-cis retinoic acid as described in the Example section. Point mutants consist of amino acids 197–462 of RXR. RXR197–443 represents the τc truncation. Note the difference in scale between A and B.

As shown in FIG. 3B, a positive and ligand-dependent interaction can be detected between TBP-V237G and a single RXR τc domain mutant, M454A/L455A. Although the interaction detected between TBP-V237G and RXR-M454A/L455A is weak relative to the wildtype interaction, an approximate 10-fold ligand-dependent induction of the interaction is observed (FIG. 3B). Rescue of the RXR-TBP interaction by combining a RXR τc domain mutant with a TBP mutant strongly suggests the RXR-TBP interaction detected in the two-hybrid assay results from a direct protein-protein interaction and is not mediated by a third factor.

While the invention has been described in detail with reference to certain preferred embodiments thereof, it will be understood that modifications and variations are within the spirit and scope of that which is described and claimed.

That which is claimed is:

1. A method to identify compounds which are agonists or antagonists for retinoid X receptor (RXR), said method comprising:
   contacting in a first assay:
   a first fusion protein comprising a GAL4 DNA binding domain, operatively associated with a transactivation dependent, ligand dependent component of the basal transcription machinery,
   a second fusion protein comprising a GAL4 activation domain, operatively associated with the RXR ligand binding domain,
   a putative agonist or antagonist for RXR, and
   a reporter construct comprising a GAL4 response element operatively linked to a reporter gene;
   contacting in a second assay:
   a third fusion protein comprising a GAL4 DNA binding domain, operatively associated with a transactivation independent, ligand dependent component of the basal transcription machinery,
   said second fusion protein,
   a putative agonist or antagonist for RXR, and
   said reporter construct; and thereafter
   identifying those compounds which induce transactivation in both said first assay and said second assay as agonists for RXR,
   identifying those compounds which induce transactivation in said second assay, but not in said first assay as antagonists for RXR, and
   identifying those compounds which fail to induce transactivation in either said first assay or said second assay as neither agonists nor antagonists of RXR.

2. A method according to claim 1 wherein said transactivation dependent, ligand dependent component of the basal transcription machinery is TBP.

3. A method according to claim 2 wherein said transactivation independent, ligand dependent component of the basal transcription machinery is TAF110.

4. A method to identify compounds which are agonists or antagonists for retinoid X receptor (RXR), said method comprising:
   contacting in a first assay:

a first fusion protein comprising a GAL4 DNA binding domain, operatively associated with the RXR ligand binding domain, a second fusion protein comprising a GAL4 activation domain, operatively associated with a transactivation dependent, ligand dependent component of the basal transcription machinery, a putative agonist or antagonist for RXR, and a reporter construct comprising a GAL4 response element operatively linked to a reporter gene;

contacting in a second assay:

a third fusion protein comprising a GAL4 DNA binding domain, operatively associated with a transactivation independent, ligand dependent component of the basal transcription machinery, said second fusion protein, a putative agonist or antagonist for RXR, and said reporter construct; and thereafter identifying those compounds which induce transactivation in both said first assay and said second assay as agonists for RXR, identifying those compounds which induce transactivation in said second assay, but not in said first assay as antagonists for RXR, and identifying those compounds which fail to induce transactivation in either said first assay or said second assay as neither agonists nor antagonists of RXR.

5. A method according to claim 4 wherein said transactivation dependent, ligand dependent component of the basal transcription machinery is TBP.

6. A method according to claim 5 wherein said transactivation independent, ligand dependent component of the basal transcription machinery is TAF110.

7. A method to identify compounds which are agonists for retinoid X receptor (RXR), said method comprising:

contacting in a host cell:

a first fusion protein comprising a GAL4 DNA binding domain, operatively associated with a transactivation dependent, ligand dependent component of the basal transcription machinery, a second fusion protein comprising a GAL4 activation domain, operatively associated with the RXR ligand binding domain, a putative agonist for RXR, and a reporter construct comprising a GAL4 response element operatively linked to a reporter gene;

thereafter, identifying those compounds which induce transactivation in the presence of said transactivation dependent, ligand dependent component of the basal transcription machinery as agonists for RXR.

8. A method to identify compounds which are neither agonists nor antagonists for retinoid X receptor (RXR), said method comprising:

contacting:

a first fusion protein comprising a GAL4 DNA binding domain, operatively associated with a transactivation independent, ligand dependent component of the basal transcription machinery, a second fusion protein comprising a GAL4 activation domain, operatively associated with the RXR ligand binding domain, a putative agonist or antagonist for RXR, and a reporter construct comprising a GAL4 response element operatively linked to a reporter gene;

identifying those compounds which fail to induce transactivation in the presence of said transactivation independent, ligand dependent component of the basal transcription machinery as neither agonists nor antagonists for RXR.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CGGAGGACTG TCCTCCG                                                        17

(2) INFORMATION FOR SEQ ID NO:2:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

AGGACAAAGG TCA                                                            13

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GGACCAGGAC AAAGGTCACG TTC                                                 23